(12) United States Patent
Willette

(10) Patent No.: US 7,704,463 B2
(45) Date of Patent: Apr. 27, 2010

(54) LOW VOLTAGE ULTRAVIOLET HVAC LIGHT

(76) Inventor: Christopher A. Willette, 3421 Harbor Rd. South, Tequesta, FL (US) 33469

( * ) Notice: Subject to any disclaimer, the term of this patent is extended or adjusted under 35 U.S.C. 154(b) by 583 days.

(21) Appl. No.: 11/656,343

(22) Filed: Jan. 22, 2007

(65) Prior Publication Data

US 2007/0202021 A1 Aug. 30, 2007

Related U.S. Application Data

(60) Provisional application No. 60/760,470, filed on Jan. 20, 2006.

(51) Int. Cl.
*B01J 19/12* (2006.01)
(52) U.S. Cl. .................. 422/186.3; 96/16; 96/224; 422/108
(58) Field of Classification Search .......... 96/224, 96/16; 422/108, 186.3
See application file for complete search history.

(56) References Cited

U.S. PATENT DOCUMENTS

| | | | | |
|---|---|---|---|---|
| 2,651,383 A * | 9/1953 | Yonkers, Jr. | .................. | 96/16 |
| 3,403,252 A * | 9/1968 | Nagy | .................. | 361/231 |
| 3,745,750 A * | 7/1973 | Arff | .................. | 96/16 |
| 4,006,354 A * | 2/1977 | deVos et al. | .................. | 362/296.05 |
| 4,404,865 A * | 9/1983 | Kim | .................. | 74/471 XY |
| 5,152,814 A * | 10/1992 | Nelson | .................. | 96/224 |
| 5,490,470 A * | 2/1996 | House | .................. | 111/186 |
| 5,601,786 A * | 2/1997 | Monagan | .................. | 422/108 |
| 6,078,712 A * | 6/2000 | Tschope et al. | .................. | 385/101 |
| 6,536,919 B1 * | 3/2003 | Johnson et al. | .................. | 362/265 |
| 6,543,282 B1 * | 4/2003 | Thompson | .................. | 73/204.15 |
| 6,585,809 B1 * | 7/2003 | Parsa | .................. | 96/16 |
| 7,318,856 B2 * | 1/2008 | Taylor et al. | .................. | 96/16 |
| 2002/0191400 A1 * | 12/2002 | Jilk et al. | .................. | 362/257 |
| 2003/0127506 A1 * | 7/2003 | Braun, Jr. | .................. | 232/31 |
| 2004/0007134 A1 * | 1/2004 | Parsa | .................. | 96/16 |
| 2004/0226447 A1 * | 11/2004 | Lau et al. | .................. | 96/16 |
| 2005/0000365 A1 * | 1/2005 | Nelsen et al. | .................. | 96/224 |
| 2005/0286265 A1 * | 12/2005 | Zampini et al. | .................. | 362/612 |
| 2006/0096459 A1 * | 5/2006 | Iwano et al. | .................. | 96/224 |

* cited by examiner

*Primary Examiner*—Robert J Hill, Jr.
*Assistant Examiner*—Christopher P Jones
(74) *Attorney, Agent, or Firm*—Michael K. Dixon; Akerman Senterfitt

(57) ABSTRACT

This UV light system for use in a central air handling unit of a heating or air conditioning system includes a UV light source and is adapted for operation on, and receives power from, an approximately 24VAC low voltage power supply for a thermostat of the heating or air conditioning system. In its preferred embodiments it is provided with a mounting system including a bendable "Z" shaped mounting bracket, which bracket can be bent to multiple angles allowing the UV light source to be positioned in numerous ways within the central air handling unit. It is preferably packaged in a cylindrical packing case where the elongate cylindrical emitter portion of the UV light source is aligned with the axis of the case.

18 Claims, 12 Drawing Sheets

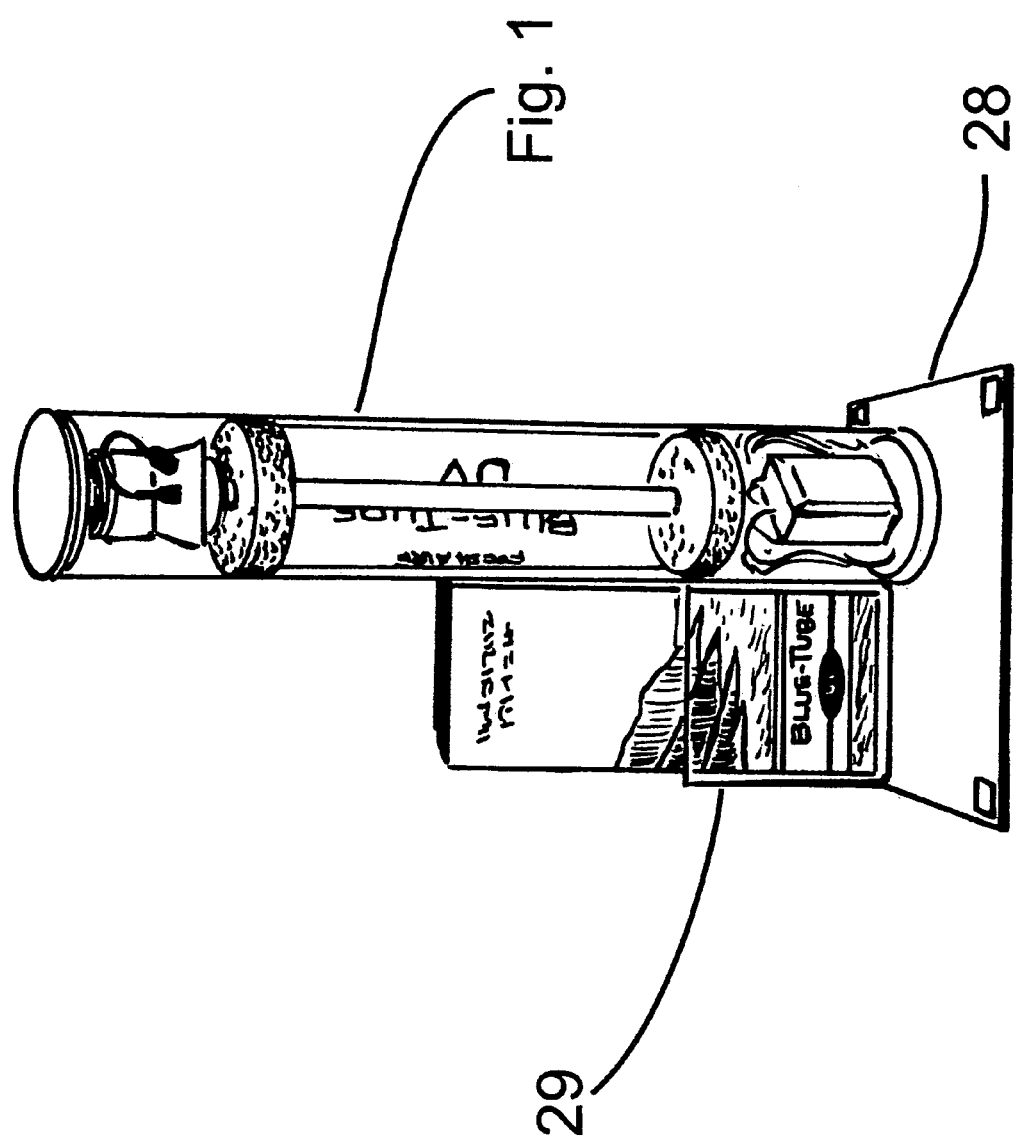

LOW VOLTAGE ULTRAVIOLET HVAC LIGHT

CROSS-REFERENCE TO RELATED APPLICATIONS

This application claims an invention which was disclosed in a provisional application filed Jan. 20, 2006, entitled "Low Voltage Ultraviolet Light Apparatus and Packing" and assigned Ser. No. 60/760,470. The benefit under 35 USC §119(e) of the U.S. provisional application is hereby claimed, and the aforementioned application is hereby incorporated herein by reference.

BACKGROUND AND SUMMARY

The present invention relates to a low voltage ultraviolet light apparatus for application into typical centralized air heating, ventilating and air conditioning (HVAC) systems. The device is intended for the reduction and control of organic contamination that can occur within confines of these central air handling units (AHU's).

Organic contamination such as algal, fungal, bacterial, and viral contamination of central air handling units (AHU's) components is a widespread indoor air related problem in homes and buildings with centralized heating, ventilation, and air-conditioning (HVAC) systems and is a potential source of contamination of the occupied air space. Organic growth has been found growing on air filters, insulation, internal wires, blower wheels and motors, cooling coils, and drain pans as well as in ducts of these systems. This contamination if un-checked can contribute to building-related illnesses and diseases, including both infectious diseases and hypersensitivity diseases.

By applying the present inventions ultraviolet light apparatus into typical central air handling units (AHU's), it can help to maintain components that are susceptible to organic growth and fouling through the use of the germicidal ultraviolet light, which can prevent the organic fouling from occurring and spreading.

The present invention includes a low voltage ultraviolet light apparatus (including its means for attachment) and it's related packaging for marketing. As discussed in more detail below, the ultraviolet light apparatus also involves an extended operating range low voltage power supply, weather resistant lamp cable, weather resistant lamp and related mounting hardware. Further, as also discussed in more detail below, the packing of the ultraviolet light for transport and marketing involves a tube that contains two end caps to contain the product within the tube's interior, a paper insert that contains marketing and technical information on the UV apparatus and two round foam inserts that pad and contain the UV apparatus components on either end, with the UV light source aligned with and within the tube's center.

The low voltage power supply of my invention is intended to receive it's power source from the 24 VAC low voltage source that is commonly found within residential air and light commercial air handling units (AHU's). This power source is typically the source that powers the thermostat and controls of the air handling unit. However, its use is difficult in this application both because it must be made compatible with the normal demand for 60 VAC used to power the UV light source and because the low voltage source for thermostat power is itself subject to great variation in terms of output, often ranging from 18 to 32 VAC.

A weather resistant lamp cable is attached to the low voltage power supply. This cable is intended to supply power to the ultraviolet light source and is weather resistant due to the inherent moist nature found within typical air handling units.

The weather resistant ultraviolet light source is intended to be applied to various configurations of air handling units for the purpose of disinfection and sterilization of internal components that are prone to grow organic microbial contaminates.

The present invention also involves a method for the reduction of typical indoor odors through a combination of ultraviolet light spectrums emitted by the UV light source. The combination of UV spectrums produces a UV oxidative effect that increases the UV's reactivity with odors and other volatile organic compounds (VOC's).

The present invention likewise involves an installation hardware kit for mounting the ultraviolet light apparatus within typical air handling units. The installation hardware kit includes a specially designed magnetic "Z" bracket for the purpose of mounting the ultraviolet light source above the components of the air handling unit.

Finally, The present invention involves special packaging and display innovations. These relate to case packing of the product for display and marketing of a bulk quantity of the product. The case packaging involves a cardboard case box for boxing multiples of the product, such as a case containing 15 pieces. In addition the case packaging involves a marketing display such as a poster attached to the outside of the case box. Further, a lighted counter display unit allows visual display and marketing of the product. The counter display involves a working and lighted sample of the UV apparatus and it's related packaging that is attached to a flat counter mountable base. Additionally, a retail brochure holder can be attached to this base for the purpose of displaying the sales and marketing credentials of the UV apparatus.

BRIEF DESCRIPTION OF THE DRAWINGS

FIG. 7 provides a perspective view of the counter display of the invention.

DESCRIPTION

Figure 1:
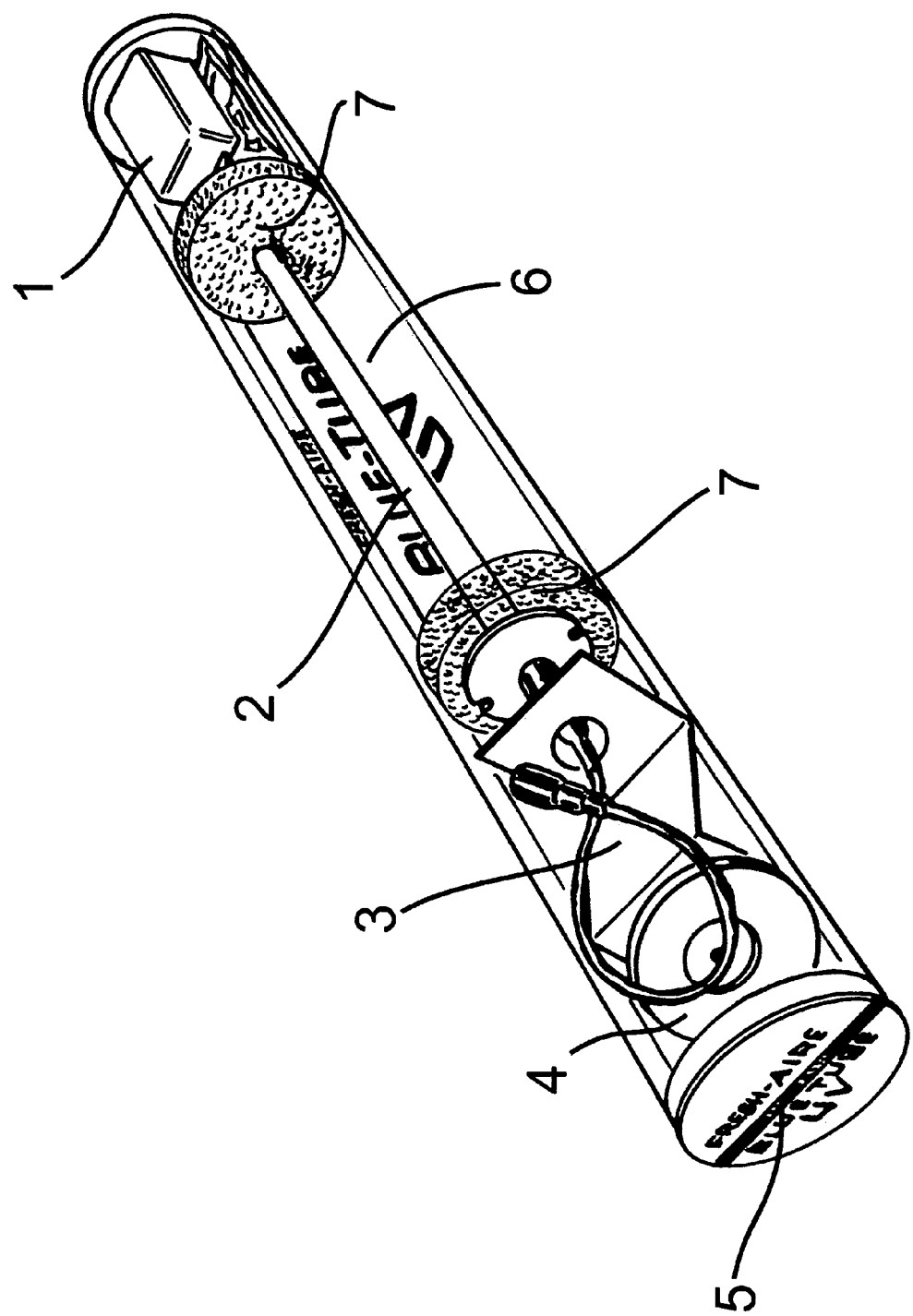
FIG. 1 provides a first perspective view of the ultraviolet light apparatus and the related transparent packaging cylinder or tube of my invention.

FIG. 1 provides an illustration of the UV apparatus and related packing. The UV apparatus 1, 2, 3 has been placed inside of a clear tubular package 4 for the intention of display and marketing. The clear packaging 4 serves two main purposes for the invention. First, it serves as a means to quickly and easily display the UV apparatus for marketing and sale. Second, it serves as a means to transport the UV apparatus prior to installation. The tube contains two end caps 5 to contain the product within the tube's interior, a paper insert 6 that contains marketing and technical information on the UV apparatus and two round foam inserts 7 that contain the UV apparatus components on either end 1 and 3, and the UV light source 2 within the tube's center.

Figure 2A:
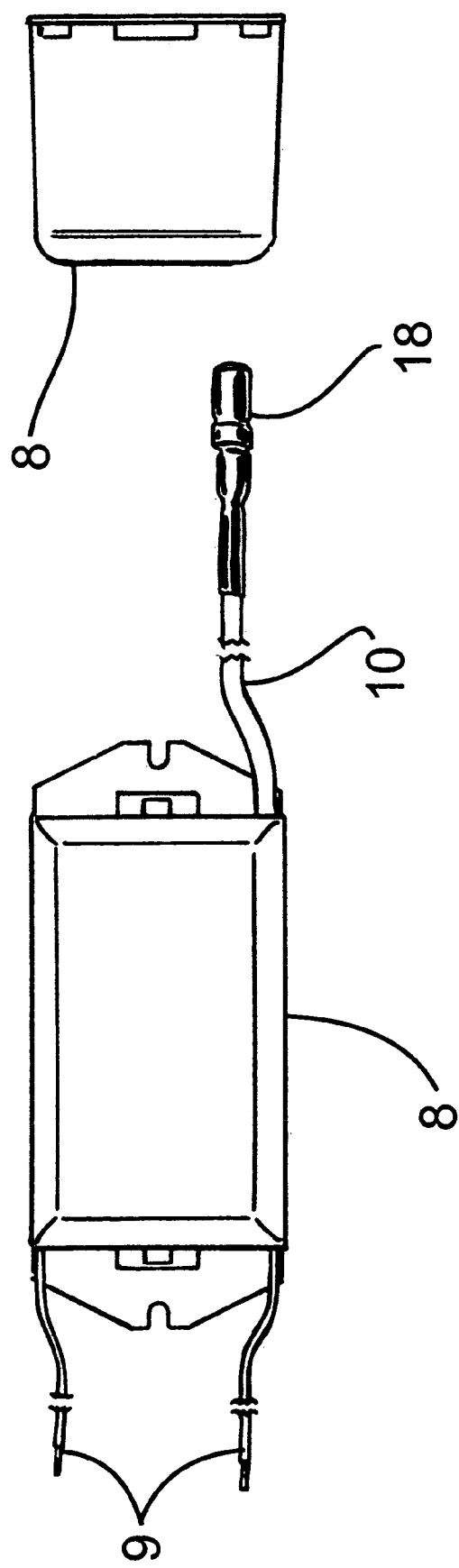
FIGS. 2A through 2C provide illustrations of the low voltage power supply of my invention and its related wire harnesses.
Figure 2B:
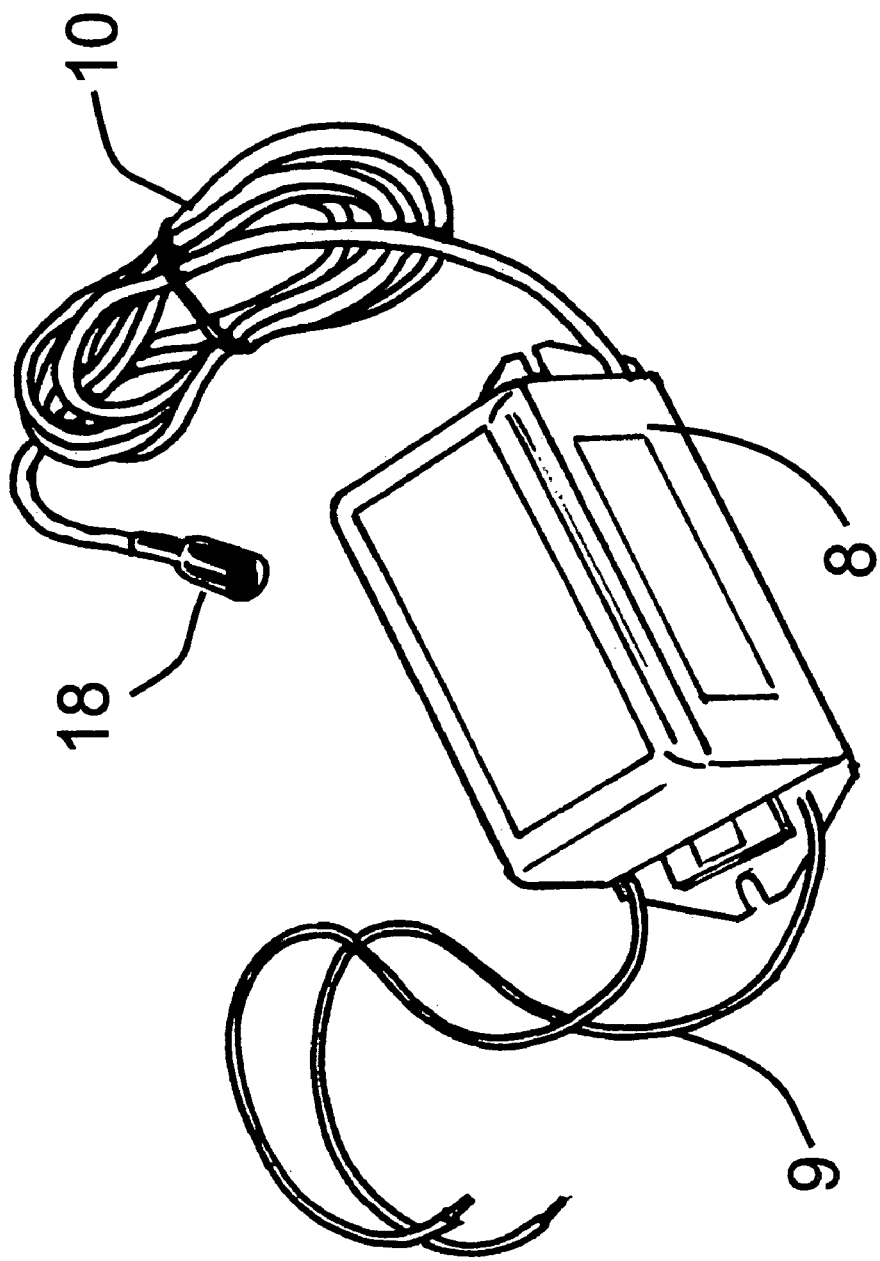
Figure 2C:
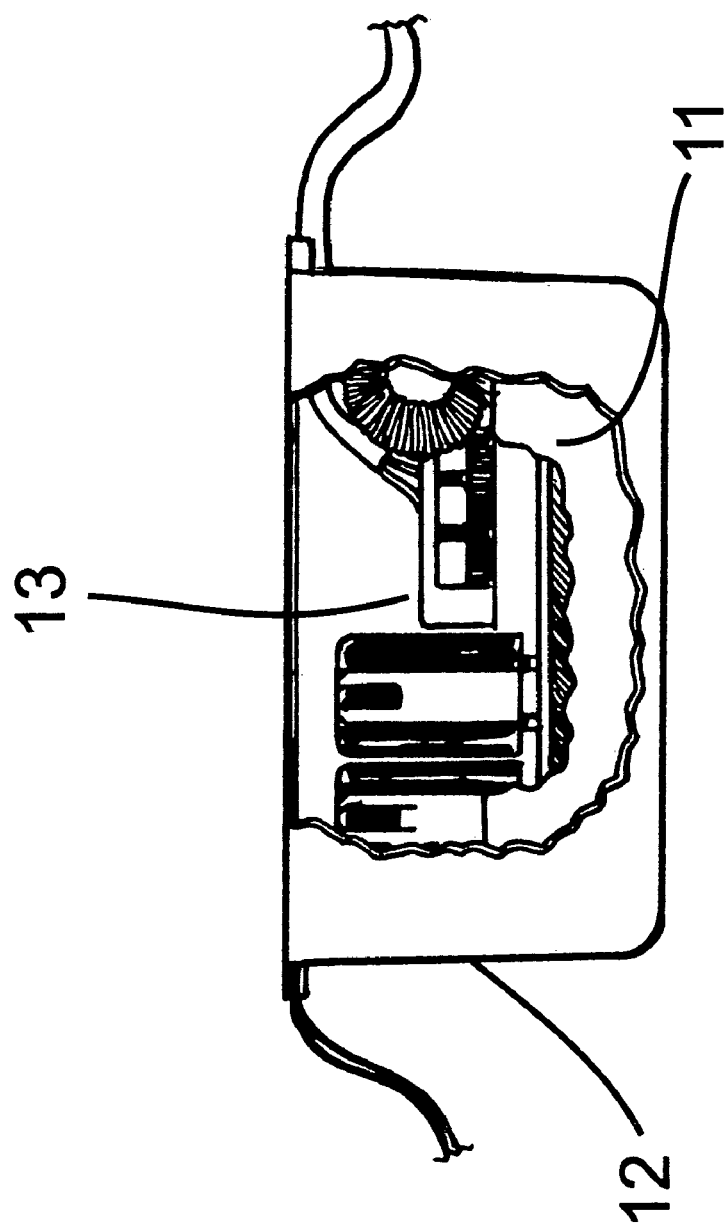

FIGS. 2A through 2C illustrate the low voltage power supply 8 and it's related wire harnesses 9 and 10. The power supply 8 is comprised of a low voltage electronic circuit 11 designed to operate the UV light source 2. The circuit 11 has been specially designed to except an extended range of low voltage supply voltages that range from eighteen (18) volts of alternating current (VAC) up to thirty-two (32) volts (VAC). The extended range low voltage power supply 8 is intended to receive it's power source from the twenty-four (24) VAC low voltage source found within typical residential air and light commercial air handling units (AHU's). This power source is typically the source that powers the thermostat and controls of the air handling unit and is fed from a low voltage transformer that takes the high voltage from the main power supply of the air handling unit and transformers it to a low voltage range for this purpose. It is not uncommon for this source of power to be inconsistent and not exactly at twenty-four VAC. In fact, it is made even more difficult to use for the purposes of this invention as it is typical to find this voltage source to have varying degrees of voltages within the eighteen to thirty-two VAC range. Moreover, the UV light source 2 requires approximately 60 VAC.

However, subject to overcoming these problems, this voltage source is an attractive source of power to be used for this invention and for the purpose of powering this type of UV light apparatus 1, 2, 3 because it is a common source of power found throughout the air conditioning industry, regardless of manufacturer of AHU. Therefore, in the case of this invention, it has been a particular point of non-obvious innovation to include and use a circuit 11 designed to accept these low and varying voltages. The principle behind circuit 11 is known generally to those in the electronic arts as the Villard's cascade and, in addition to a band pass filter, provides the foundation for the design of Circuit 11.

The usual power conditioning method for using a low voltage source in an operation of this type would be to incorporate a voltage doubler circuit on the incoming power in the circuit design. This would seem to be an acceptable method as the UV light source will typically operate between 40 and 60 volts of operating voltage. Thus, a typical voltage doubler circuit could take the incoming power source of 24 VAC and double it to 48 VAC. However, when the incoming power is inconsistent (as in the current application) then the doubling effect can magnify the power problems associated with it and give inconsistent operating voltages which can cause increased operating heat loads on circuit components and potential product failure.

Thus, I use a full wave voltage multiplier circuit with a band pass filter which actually involves multiple voltage doublers and band pass filters that allow the inconsistent power to be multiplied and then filtered several times to provide a stabilized operating voltage at a more normalized level. In my invention, circuit 11 first doubles the input voltage from 24 to 48 VAC and then filters it within an acceptable operating range. It then takes another input voltage of 24 VAC, doubles it again, filters it again, and averages the two values together with a capacitor to provide a more stabilized averaged value.

From review of the foregoing, it is clear that circuit 11 has been designed to optimize operation of the UV light source 2 for it's maximum efficiency under these low voltage and varying conditions. Also, the circuit 11 is intended to be used in damp environments that can damage the circuit if not protected. For this reason, the circuit 11 is encased in a "potted" enclosure 12 where the circuit board is placed inside of a plastic case 12 and coated and secured within the inside of the case with a weather resistant "potting" material.

The power supply 8 contains a pair of incoming power leads 9, one red and one black for connection to the low voltage supply source. Also, the power supply 8 contains a weather resistant lamp supply cable 10 for connection to the UV light source 2. This supply cable 10 is designed to be weather resistant because the operating conditions in which the UV apparatus 1, 2, 3 is applied is often times in highly wet or damp conditions found within the interior of air handling units that could damage the cables operation otherwise.

Figure 3A:
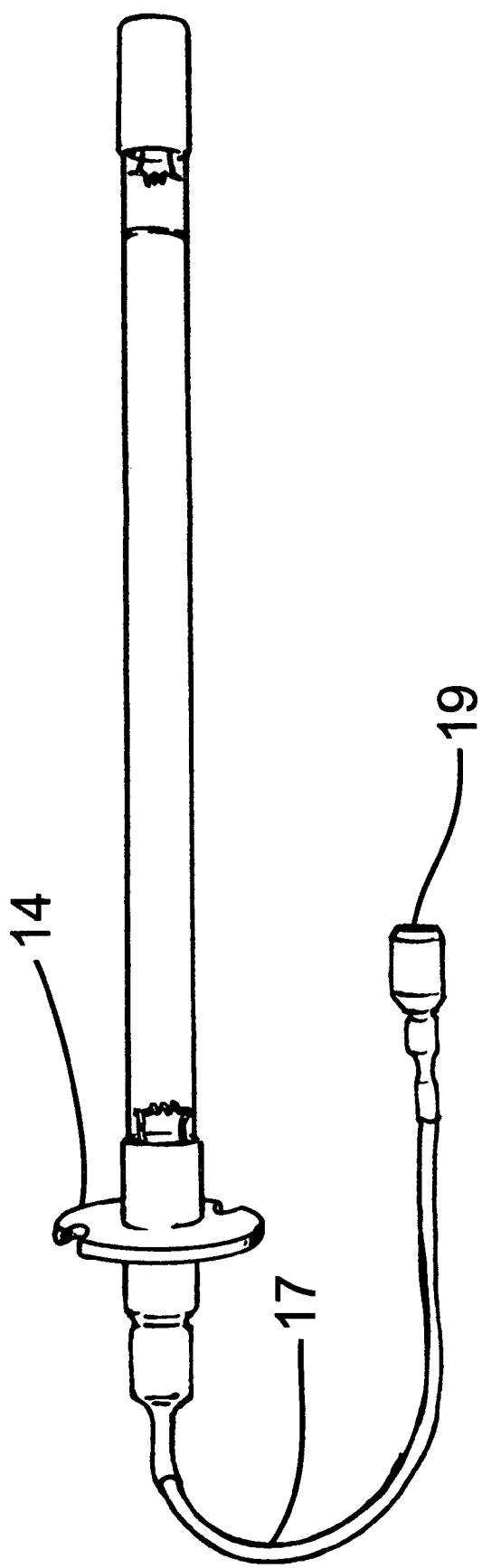
FIGS. 3A through 3C provide perspective views of the weather resistant ultraviolet light source of my invention, including its base and installation variations.
Figure 3B:
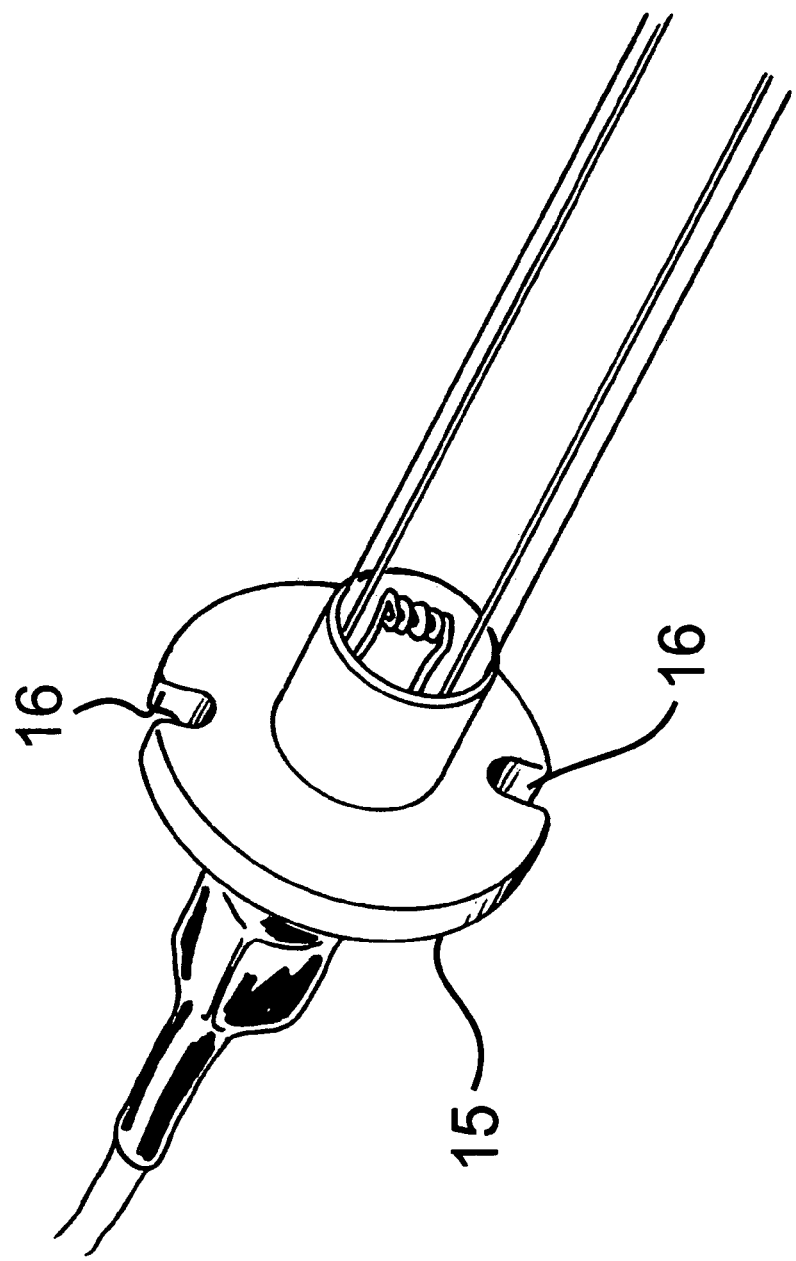
Figure 3C:
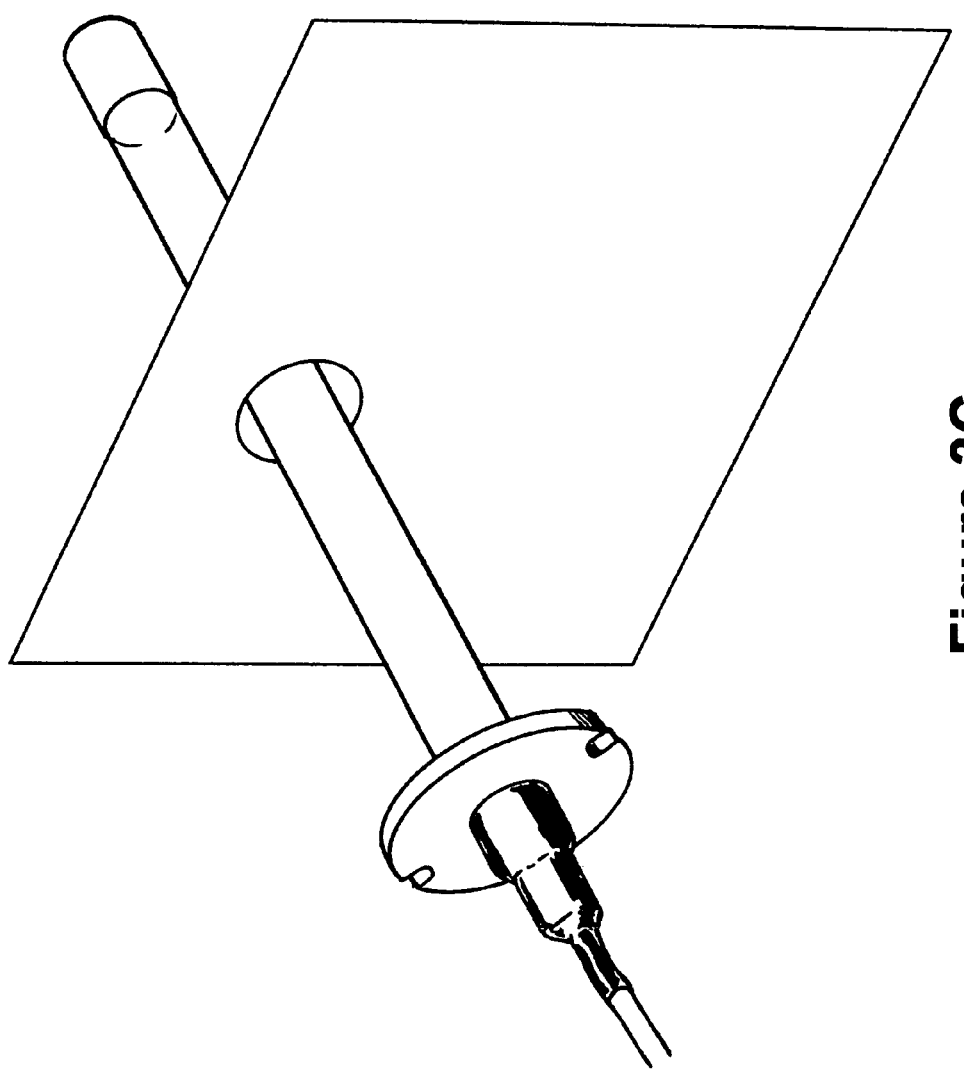

FIGS. 3A through 3C provide further illustrations of the weather resistant ultraviolet light source 2 of my invention. The ultraviolet light source (UV Lamp) 2 is a mercury vapor style of light source of such design as to produce light in the UV-C germicidal spectrums such as 254 nM. This spectrum is well documented for it's effectiveness in sterilizing microbial contaminates and is commonly used for this type of UV light source 2. Other frequencies, such as 185 nM can be incorporated into the lamp also to produce additional benefits such as odor control and are discussed with reference to FIG. 4.

The UV Lamp 2 contains a specially designed base 14 that allows for the UV lamp 2 to be applied in a number of different installation configurations. The large flat circular ring (or annular flange) 15 found around the mid point of the base 14 provides a stable surface for mounting the lamp 2. This affords the opportunity for the lamp 2 to be mounted to flat surfaces using a through hole mounting technique as illustrated in FIG. 3C or mounted to the specially designed magnetic "Z" mounting bracket of the invention (as discussed in detail with reference to FIG. 5). The base ring 15 has two U shaped cut-outs 16 that allow for mounting screws or studs to pass within the circumference area of the base ring for securing it to these surfaces.

The UV lamp 2 also contains a 12" long lamp cable "pigtail" 17 which is intended to provide a means of connecting the lamp 2 remotely from the power supply 1 of FIG. 2. This cable is designed to be weather resistant because the operating conditions in which the UV apparatus 1, 2, 3 is applied is often times in highly wet or damp conditions found within the interior of air handling units that could damage the cables operation otherwise. The particular design intention of the 12" lamp cable "pigtail" 17 is such that the lamp 2 can be connected and disconnected in the immediate location where the lamp 2 is placed. The connectors of the power supply cable 18 and lamp "pigtail" 19 are of such design as that manufactured by PEI Genesis for application in wet environments.

Figure 4:
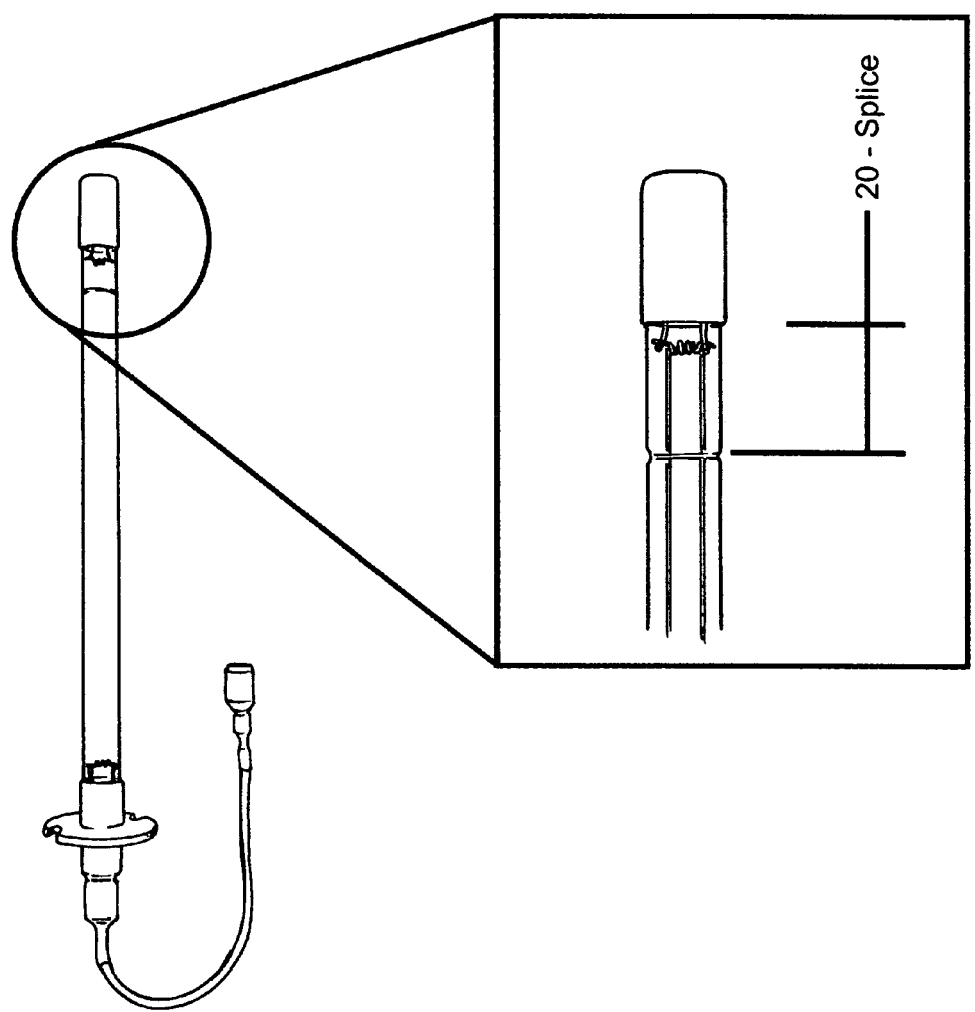
FIG. 4 provides a more detailed perspective view of the UV/Oxidation tip of the ultraviolet light source, which assists in the reduction of odors.

FIG. 4 provides a more detailed illustration of the ultraviolet light source 2 with the UV/Oxidation tip 20 for reduction of odors. As outlined in the discussion of FIGS. 3A through 3C, it is the intention of the UV light source 2 to produce light in the UV-C spectrum for the purpose of sterilization of microbial contamination. But, in addition, this UV-C light can be combined with a small segment of the lamp body to contain a "splice" 20 of the lamp to produce light in a different spectrum such as that at 185 nM in the UV-O spectrum range.

This "splice" provides additional benefits to the design of the lamp 2 such as for odor control or the reduction of volatile organic compounds (VOC's), which are chemical or organic compounds found in the air that can potentially pose health risks. The light produced in the UV-O range and particularly at 185 nM has been shown to react with oxygen and humidity in the air to produce ozone and hydroxyl radicals (OH ions), which are recognized as an oxidizing agents that can destroy odor molecules and VOC molecules. It is of particular embodiment and design of this lamp 2 to contain only a small portion of this light spectrum so therefore the lamp 2 is constructed such that no more than 10% of the lamps length is of this spectrum. And the term "splice" comes from the fact that these two sections of the lamp are "spliced" 20 or fused together at this point.

Figure 5A:
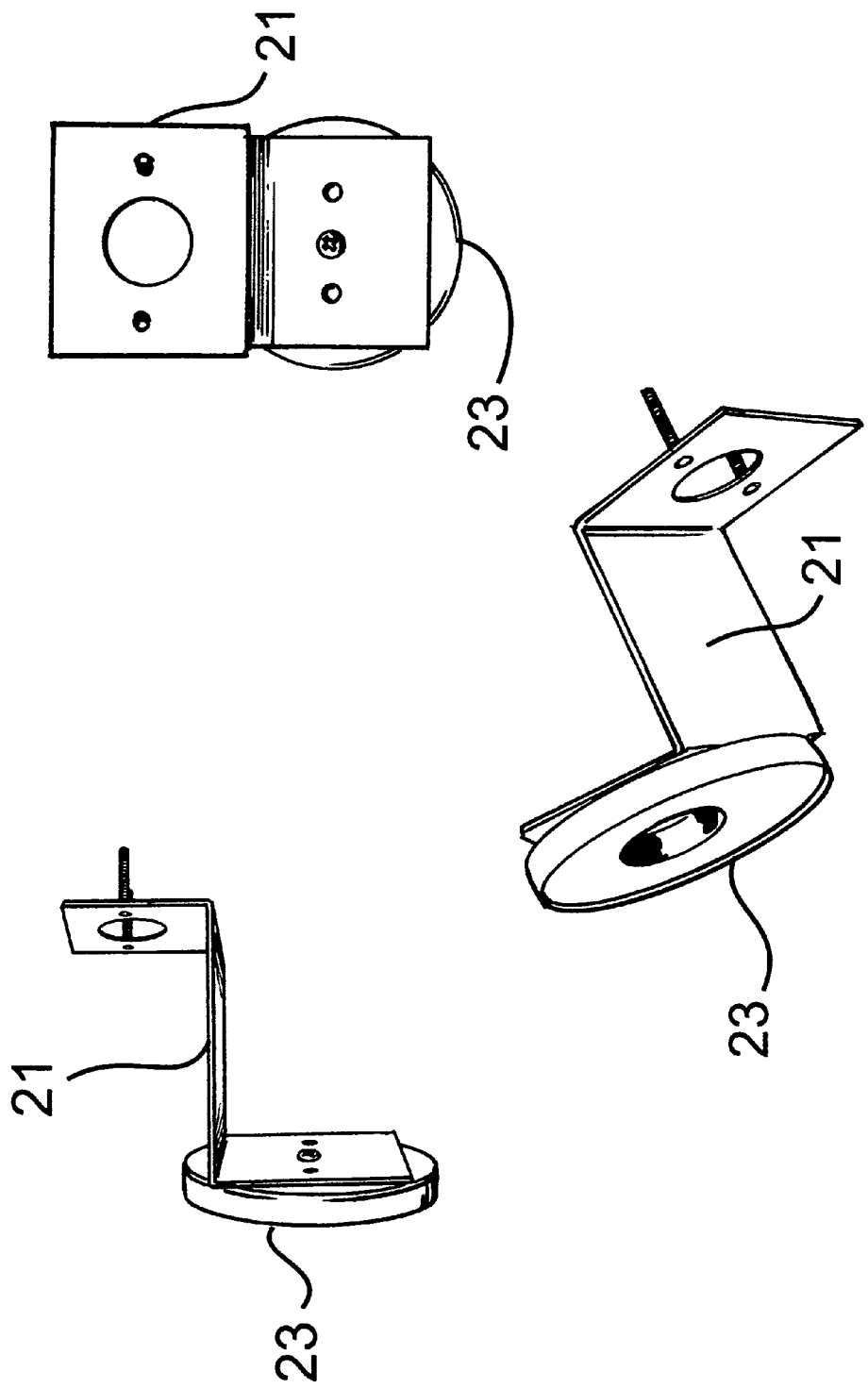
FIGS. 5A and 5B provide views of the installation hardware kit of my invention, with FIG. 5A providing separate perspective views of the "Z" shaped mounting bracket of the invention.
Figure 5B:
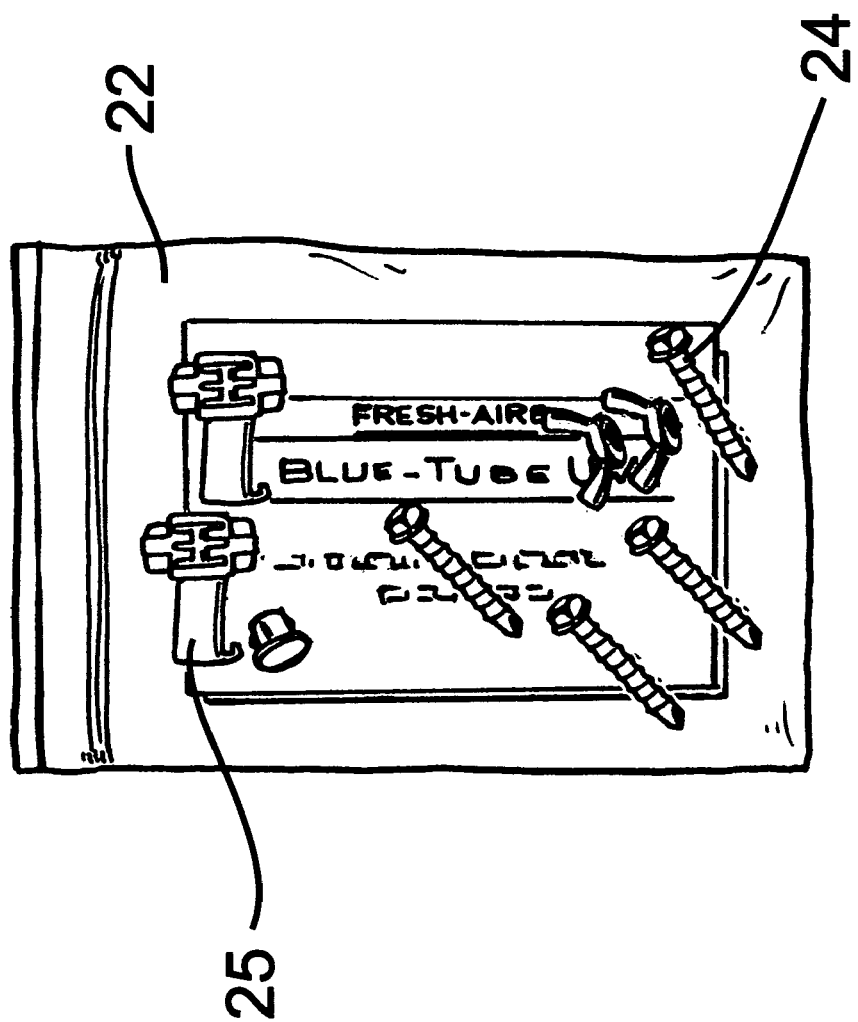

FIGS. 5A and 5B provide several illustrations of the installation hardware kit 22 and specially designed "Z" lamp mounting bracket 21. As mentioned previously, the UV apparatus 1, 2, 3 of this invention entails a extended range low voltage power supply 1 and UV light source 2 that is intended to be installed within the confines of centralized air handling units. As these air handling units (AHU's) come in many different varieties and the range of configurations of the internal components is numerous, it is important to provide the necessary hardware to properly implement the UV apparatus 1, 2, 3 for the purpose of preventing microbial contamination growth from inside of these AHU's and on all of it's internal components contained within. Of particular embodiment to this invention is the design of the "Z" mounting bracket 21, which is intended to provide a variety of mounting options for the UV lamp 2.

The "Z" mounting bracket 21 contains a magnet 23 attached to it's base such that the "Z" bracket 21 can be magnetically fixed to an interior surface of these AHU's, which are typically constructed of ferrous metal that will afford the opportunity for the magnet to become affixed to the interior metal panels of the AHU. If this is not the case, the magnet 23 can be removed from the "Z" bracket 21 and the hardware kit 22 contains self tapping sheet metal screws 24 that can be used to affix the bracket 21 to these surfaces or other internal surfaces or components of the AHU.

In addition, the "Z" bracket 21 is constructed of bendable aluminum to allow the bracket 21 to be bent to any degree of angles to allow the opportunity for the UV lamp 2 to be positioned in a varying degree of angles for optimum exposure of the UV light to the surfaces intended for exposure. In essence, the "Z" mounting bracket 21 is a universal mounting apparatus intended to give the maximum amount of mounting opportunities to the installer to achieve the optimum exposure potential of the UV light source 2.

If it is not feasible to use the "Z" mounting bracket 21 then the particular design of the lamps base (as described with reference to FIG. 3B) is utilized. In this case, a 1" hole can be drilled into any flat surface of the AHU such as the A-plate of the AHU's coil or one of the exterior panels of the AHU. The lamp is then secured using a set of the included self tapping sheet metal screws 24 of the hardware kit 22. Additionally, the hardware kit 22 contains wire attachments that allow for the low voltage power supplies 1 power input wires 9 to be connected to the low voltage wires found inside of the AHU.

Figure 6:
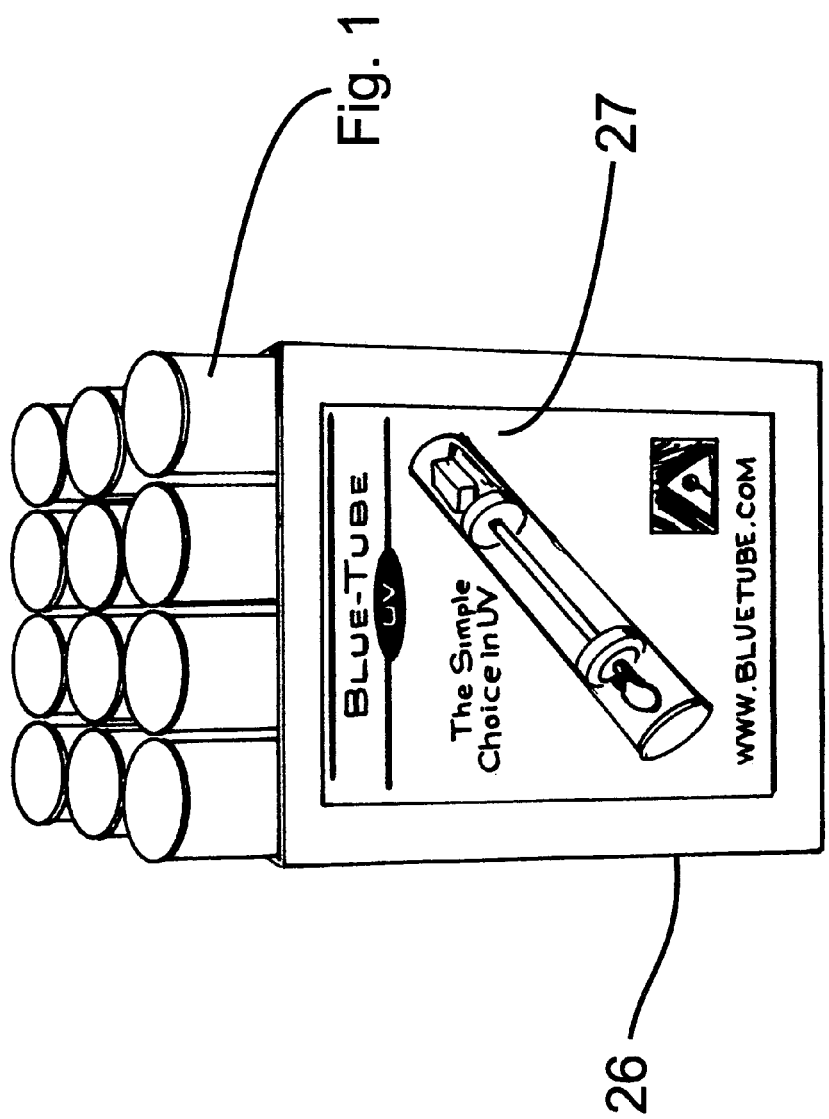
FIG. 6 provides a perspective view of the case box packaging of the invention.

FIG. 6 provides an illustration of the case packing of the present invention. As the design of the UV apparatus's packing of FIG. 1 is for a point of sale display marketing concept, the apparatus 1, 2, 3 when displayed in bulk is intended to also convey the point of sale approach. Therefore, the case packaging 26 is design to hold a bulk quantity of fifteen units and has been designed to hold the packages in a vertical arrangement such that the bar code and model number of the UV apparatus's package of FIG. 1 can be displayed. Additionally, the outer face of the case packaging contains a marketing point of sales poster 27 that explains the UV apparatus and it's features and benefits.

FIG. 7 provides an illustration of the counter display of the present invention. As the design of the UV apparatus's packing of FIG. 1 is for a point of sale display marketing concept, the apparatus itself when displayed can also convey the point of sale approach. In this case, a sample of the UV apparatus and it's related packaging of FIG. 1 can be attached to a flat counter mountable base 28 that can be modified to light up non UV-C producing light source for display purposes only for the purpose of drawing attention to the product for point of sales marketing purposes. Additionally, a retail brochure holder 29 can be attached to this base for the purpose of displaying the sales credentials of the UV apparatus.

Thus, as should be clear from the foregoing, my invention includes any or all of the foregoing features, either alone or in combination:

(a) A UV apparatus designed to operate off of the low voltage (24 VAC) control circuit power supply of typical centralized air handling units.

(b) A UV light power supply designed to operate within an extended range of low voltage supply voltages that range from eighteen (18) volts of alternating current (VAC) up to thirty-two (32) volts (VAC).

(c) A UV light power supply circuit designed to optimize the operation of the UV light source for it's maximum efficiency under these low voltage and varying conditions.

(d) A UV power supply circuit intended to be used in damp environments that can damage the circuit if not protected, therefore the circuit is encased in a "potted" enclosure where the circuit board is placed inside of a plastic case and coated and secured within the inside of the case with a weather resistant "potting" material.

(e) A UV power supply containing a pair of incoming power leads, one red and one black for connection to the low voltage supply source.

(f) A UV power supply containing a weather resistant lamp supply cable for connection to the UV light source.

(g) An ultraviolet light source to be applied to the interior of central air handling units for the control of surface and airborne microbial contamination from within the interior components of these units.

(h) An ultraviolet light source (UV Lamp) of mercury vapor type of light source of such design as to produce light in the UV-C germicidal spectrums such as 254 nM.

(i) An ultraviolet light source (UV Lamp) of mercury vapor type of light source of such design as to produce light in the 185 nM to produce additional benefits such as odor control.

(j) A ultraviolet light source with the UV/Oxidation tip for reduction of odors.

(k) A UV light source that contains a "splice" of the lamp to produce light in a different spectrum such as that at 185 nM in the UV-O spectrum range.

(l) A UV light source that contains only a small portion of this light spectrum so therefore the lamp is constructed such that no more than 10% of the lamps length is of this spectrum.

(m). An ultraviolet light source that contains a specially designed base that allows for the UV lamp to be applied in a number of different installation configurations.

(n) A UV lamp mounting base that contains a large flat circular ring (or annular flange) found around the mid point of the base that provides a stable surface for mounting the lamp.

(o) A UV lamp that contains a 12" long lamp cable "pigtail" which is intended to provide a means of connecting the lamp remotely from the power supply.

(p) A specially designed "Z" mounting bracket intended to provide a variety of mounting options for the UV light source of this invention.

(q) A "Z" mounting bracket that contains a magnet attached to it's base such that the "Z" bracket can be magnetically fixed to interior wall surfaces of AHU's, which are typically constructed of ferrous metal that will afford the opportunity for the magnet to become affixed to the interior metal panels of the AHU.

(r) A "Z" mounting bracket that, when the magnet is removed from the bracket, can be secured to interior wall surfaces of AHU's or other internal surfaces or components of the AHU with self tapping sheet metal screws.

(s) A "Z" mounting bracket constructed of bendable aluminum to allow the bracket to be bent to any degree of angles to allow the opportunity for the UV lamp to be positioned in a varying degree of angles for optimum exposure of the UV light to the surfaces intended for exposure.

(t) A "Z" mounting bracket that is a universal mounting apparatus intended to give the maximum amount of mounting opportunities to the installer to achieve the optimum exposure potential of the UV light source.

(u) If it is not feasible to use the "Z" mounting bracket than the particular design of the lamps base as described in FIG. 3B is utilized. In this case, a 1" hole can be drilled into any flat surface of the AHU such as the A-plate of the AHU's coil or one of the exterior panels of the AHU. The lamp is then secured using a set of the included self tapping sheet metal screws of the hardware kit.

(v) A UV apparatus that is placed inside of a clear tubular package for the intention of display and marketing.

(w) A UV apparatus that is placed inside of a clear tubular package as a means to quickly and easily display the UV apparatus for marketing and sale.

(x) A UV apparatus that is placed inside of a clear tubular package as a means to transport the UV apparatus prior to installation.

(y) A UV apparatus that is placed inside of a clear tubular package that contains two end caps to contain the product within the tubes interior.

(z) A UV apparatus that is placed inside of a clear tubular package that contains a paper insert that contains marketing and technical information on the UV apparatus.

(aa) A UV apparatus that is placed inside of a clear tubular package that contains two round foam inserts that contain the UV apparatus components on either end and the UV light source within the tubes center.

(bb) A UV apparatus that is placed inside of a clear tubular package that when displayed in bulk is intended to also convey the point of sale approach.

(cc) A case packaging of the UV apparatus which is design to hold a bulk quantity of fifteen units designed to hold the packages in a vertical arrangement such that the barcode and model number of the UV apparatus's package can be displayed.

(dd) A case packaging of the UV apparatus such that the outer face of the case packaging contains a marketing point of sales poster that explains the UV apparatus and it's features and benefits.

(ee) A sample of the UV apparatus and it's related packaging that is attached to a flat counter mountable base that is lite up with a non UV-C producing light source for display purposes only for the purpose of drawing attention to the product for point of sales marketing purposes.

However, it will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. An apparatus for air purification, comprising: a UV light system for use in a central air handling unit of a heating or air conditioning system, which UV light system includes a UV light source; wherein said UV light system is adapted for operation on approximately 24 VAC low voltage power from the said heating or air conditioning system; wherein said UV light source is provided with a mounting system including a bendable "Z" shaped mounting bracket, which bracket is positionable such that the UV light source can be positioned in numerous ways within the central air handling unit.

2. The apparatus described in claim 1, wherein said UV light system includes a power supply ballast for said UV light, which power supply ballast includes an electronic circuit adapted to receive said low voltage power in a range of approximately 18 VAC to 32 VAC, and operate said UV light source thereby.

3. The apparatus described in claim 1, wherein said UV light system includes a power supply ballast for said UV light, which power supply ballast includes an electronic circuit adapted to receive said low voltage power in a range of approximately 60 VAC to operate said UV light source thereby.

4. The apparatus described in claim 3, wherein said electronic circuit is potted to preserve it from moisture conditions in a heating or air conditioning system.

5. The apparatus described in claim 1, wherein said UV light system includes a power supply ballast for said UV light, which power supply ballast includes an electronic circuit adapted to receive said low voltage power and provide approximately 60 VAC to operate said UV light source thereby.

6. The apparatus described in claim 1, wherein said electronic circuit is potted to preserve it from moisture and conditions in a heating or air conditioning system.

7. The apparatus described in claim 1, wherein said UV light source produces light in the UV-C spectrum, which special range includes light having a wavelength of 254 nm and is germicidal.

8. The apparatus described in claim 7, wherein said UV light source produces light in the OV-O spectrum, which spectral range includes light having a wavelength of 185 nm and reduces odors.

9. The apparatus described in claim 8, wherein said UV light source is constructed so that approximately no more than 10% of its production is in the UV-O spectrum.

10. The apparatus described in claim 1, wherein said UV light source produces light in the OV-O spectrum, which spectral range includes light having a wavelength of 185 nm and reduces odors.

11. The apparatus described in claim 1, wherein said bendable "Z" shaped mounting bracket can be bent to multiple angles allowing the UV light source to be positioned in numerous ways within the central air handling unit.

12. The apparatus described in claim 1, wherein the UV light source includes an elongate cylindrical portion and said apparatus for air purification includes and is incorporated into a cylindrically shaped packing case, which cylindrical shape defines a central axis, and said elongate cylindrical portion is aligned with said axis.

13. The apparatus described in claim 1, wherein said "Z" shaped mounting bracket has a base with a removable magnet, such that said "Z" shaped mounting bracket can be affixed to an inner side of a ferrous metal portion of a central air handling unit by its base using said magnet and can be affixed to an inner side of a central air handling unit by its base without using said magnet.

14. The apparatus described in claim 1, wherein said UV light source is provided with an annular mounting flange at its base, allowing the light source to be mounted directly to and through a hole in a wall of a central air handling unit and to be mounted to said "Z" shaped mounting bracket through a hole provided in an end of said "Z" shaped mounting bracket.

15. An apparatus for air purification, comprising: a UV light system for use in a central air handling unit of a heating or air conditioning system, which UV light system includes a UV light source; and wherein the UV light source includes an elongate cylindrical portion and said apparatus for air purification includes and is incorporated into a cylindrically shaped packing case, which cylindrical shape defines a central axis, and said elongate cylindrical portion is aligned with said axis; wherein said UV light system is adapted for operation on approximately 24 VAC low voltage power from the said heating or air conditioning system; and wherein said UV light source is provided with a mounting system including a bendable "Z" shaped mounting bracket, which bracket can be bent to multiple angles allowing the UV light source to be positioned in numerous ways within the central air handling unit.

16. The apparatus described in claim 15, wherein a plurality of said cylindrical packing cases can be nested side-by-side in a packing crate with an end of said cylindrical packing cases exposed.

17. The apparatus described in claim 15, wherein said UV light system includes a power supply ballast for said UV light, which power supply ballast includes an electronic circuit adapted to receive said low voltage power in a range of approximately 18 VAC to 32 VAC, and provide approximately 60 VAC to operate said UV light source thereby.

18. The apparatus described in claim 15, wherein said "Z" shaped mounting bracket has a base with a removable magnet, such that said "Z" shaped mounting bracket can be affixed to an inner side of a ferrous metal portion of a central air handling unit by its base using said magnet and can be affixed to an inner side of a central air handling unit by its base without using said magnet.

* * * * *

UNITED STATES PATENT AND TRADEMARK OFFICE
CERTIFICATE OF CORRECTION

PATENT NO. : 7,704,463 B2
APPLICATION NO. : 11/656343
DATED : April 27, 2010
INVENTOR(S) : Christopher A. Willette Page 1 of 1

It is certified that error appears in the above-identified patent and that said Letters Patent is hereby corrected as shown below:

On the Title Page

Item [76], should read:
Christopher C. Willette

Signed and Sealed this
Sixth Day of July, 2021

Drew Hirshfeld
*Performing the Functions and Duties of the*
*Under Secretary of Commerce for Intellectual Property and*
*Director of the United States Patent and Trademark Office*